US00PP28974P3

(12) United States Plant Patent
Wood

(10) Patent No.: US PP28,974 P3
(45) Date of Patent: Feb. 20, 2018

(54) ***HYDRANGEA* PLANT NAMED 'HMUPSI'**

(50) Latin Name: *Hydrangea hybrida*
Varietal Denomination: HMUPSI

(71) Applicant: Timothy Wood, Spring Lake, MI (US)

(72) Inventor: Timothy Wood, Spring Lake, MI (US)

(73) Assignee: Spring Meadow, Nursery, Inc, Grand Haven, MI (US)

( * ) Notice: Subject to any disclaimer, the term of this patent is extended or adjusted under 35 U.S.C. 154(b) by 0 days.

(21) Appl. No.: 14/999,112

(22) Filed: Mar. 30, 2016

(65) Prior Publication Data

US 2017/0290222 P1 Oct. 5, 2017

(51) Int. Cl.
*A01H 5/02* (2006.01)

(52) U.S. Cl.
USPC ..... Plt./250

(58) Field of Classification Search
USPC ..... Plt./250
See application file for complete search history.

*Primary Examiner* — Keith O Robinson
(74) *Attorney, Agent, or Firm* — Cassandra Bright

(57) ABSTRACT

A new and distinct *Hydrangea* cultivar named 'HMUPSI' is disclosed, characterized by a vibrant mophead inflorescence and strong re-blooming characteristics. Plants are semi-dwarf, compact and bloom on both old and new wood Flowering stems are exceptionally strong. The new variety is a *Hydrangea*, normally produced as an ornamental plant for containers or gardens.

2 Drawing Sheets

Figure 1:
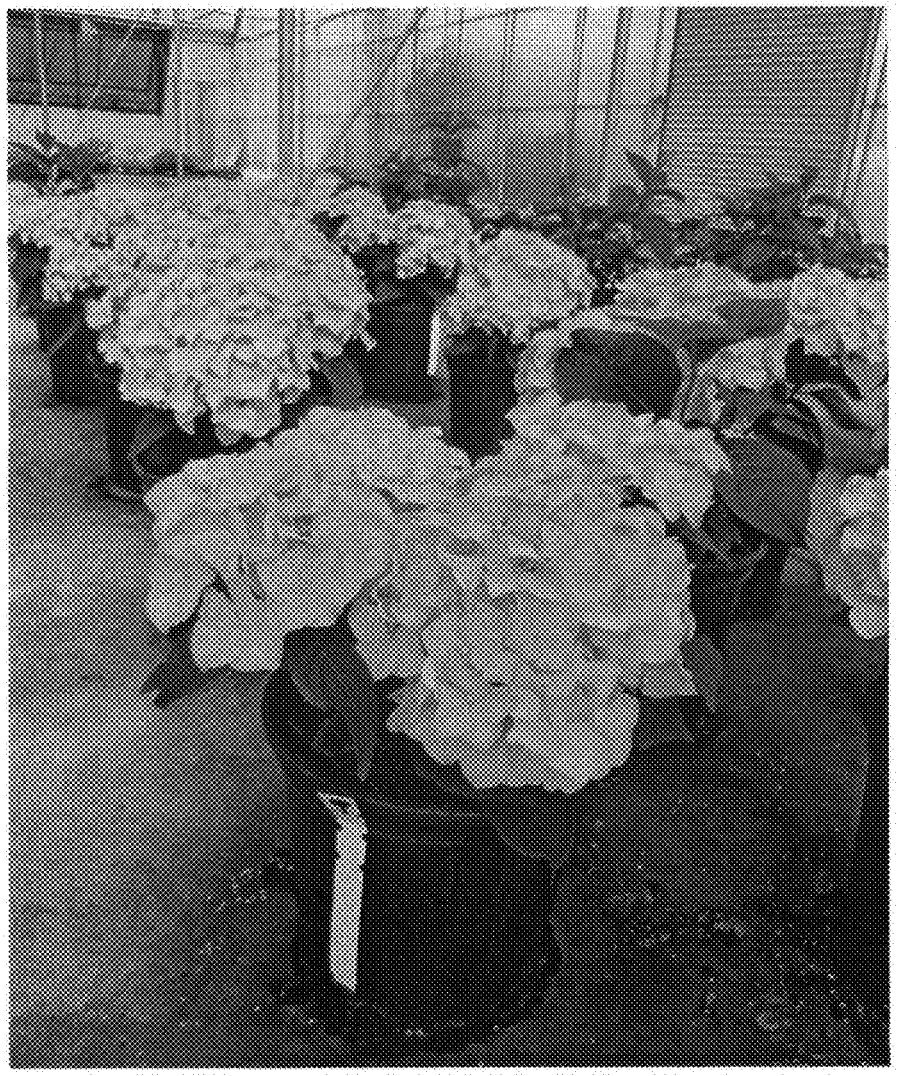

Latin name of the genus and species: *Hydrangea hybrida*.
Variety denomination: 'HMUPSI'.

BACKGROUND OF THE INVENTION

The new *Hydrangea* cultivar is a product of a planned breeding program conducted by the inventor, Timothy D. Wood, in Grand Haven, Mich. The objective of the breeding program was to produce new *Hydrangea* varieties. The open pollination resulting in this new variety was made during July of 2008.

The seed parent is the patented commercial variety *Hydrangea macrophylla* 'Robert' U.S. Plant Pat. No. 20,020. The pollen parent is unknown, as it was an open pollination breeding program. The new variety was identified as a potentially interesting selection in June of 2011, at a greenhouse in Grand Haven, Mich.

Asexual reproduction of the new cultivar 'HMUPSI' by softwood cuttings was first performed June of 2011 at a commercial greenhouse in Grand Haven, Mich. Subsequent propagation has shown that the unique features of this cultivar are stable and reproduced true to type in 4 successive generations.

SUMMARY OF THE INVENTION

The cultivar 'HMUPSI' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'HMUPSI'. These characteristics in combination distinguish 'HMUPSI' as a new and distinct *Hydrangea* cultivar:

1. Mop-head inflorescence.
2. Semi-dwarf, compact plant form.

3. Strong re-blooming habit, flowers on both old wood and new wood.
4. Vibrant colored inflorescence.
5. Strong stems hold up large inflorescence well, allowing for both good container performance as well as good garden performance.

PARENT COMPARISON

Plants of the new cultivar 'HMUPSI' are similar to plants of the seed parent, *Hydrangea macrophylla* 'Robert' in most horticultural characteristics, however, plants of the new cultivar 'HMUPSI' differ in the following:

1. The new variety has much deeper colored sepals than the parent variety, due to deeper color saturation of the sepals.
2. The new variety has even stronger re-blooming performance than the parent variety.
3. The new variety has stronger flowering stems.
4. The new variety can easily flower rich purple or violet with the application of aluminum sulfate, the parent variety will color a softer lavender-blue with the same application.

Pollen parent unknown as this is product of open pollination.

COMMERCIAL COMPARISON

'HMUPSI' can be compared to the patented commercial variety *Hydrangea* 'Berner' U.S. Plant Pat. No. 22,329. These varieties are similar in most horticultural characteristics; however 'HMUPSI' differs in the following:

1. The new variety is a significantly shorter, more compact plant.
2. The new variety has deeper sepal color saturation.
3. The new variety has smaller sepals.
4. The new variety has stronger re-blooming characteristics.

'HMUPSI' can be compared to the unpatented commercial variety *Hydrangea* 'Nikko Blue', unpatented. These varieties are similar in most horticultural characteristics; however 'HMUPSI' differs in the following:

1. The new variety is a significantly shorter, more compact plant.
2. The new variety has deeper sepal color saturation.
3. The new variety has strong re-blooming characteristics, this comparator does not rebloom.

BRIEF DESCRIPTION OF THE PHOTOGRAPHS

The accompanying photograph in FIG. 1 illustrates in full color a typical flowering plant of 'HMUPSI' grown in a greenhouse in Grand Haven, Mich., USA.

Figure 2:
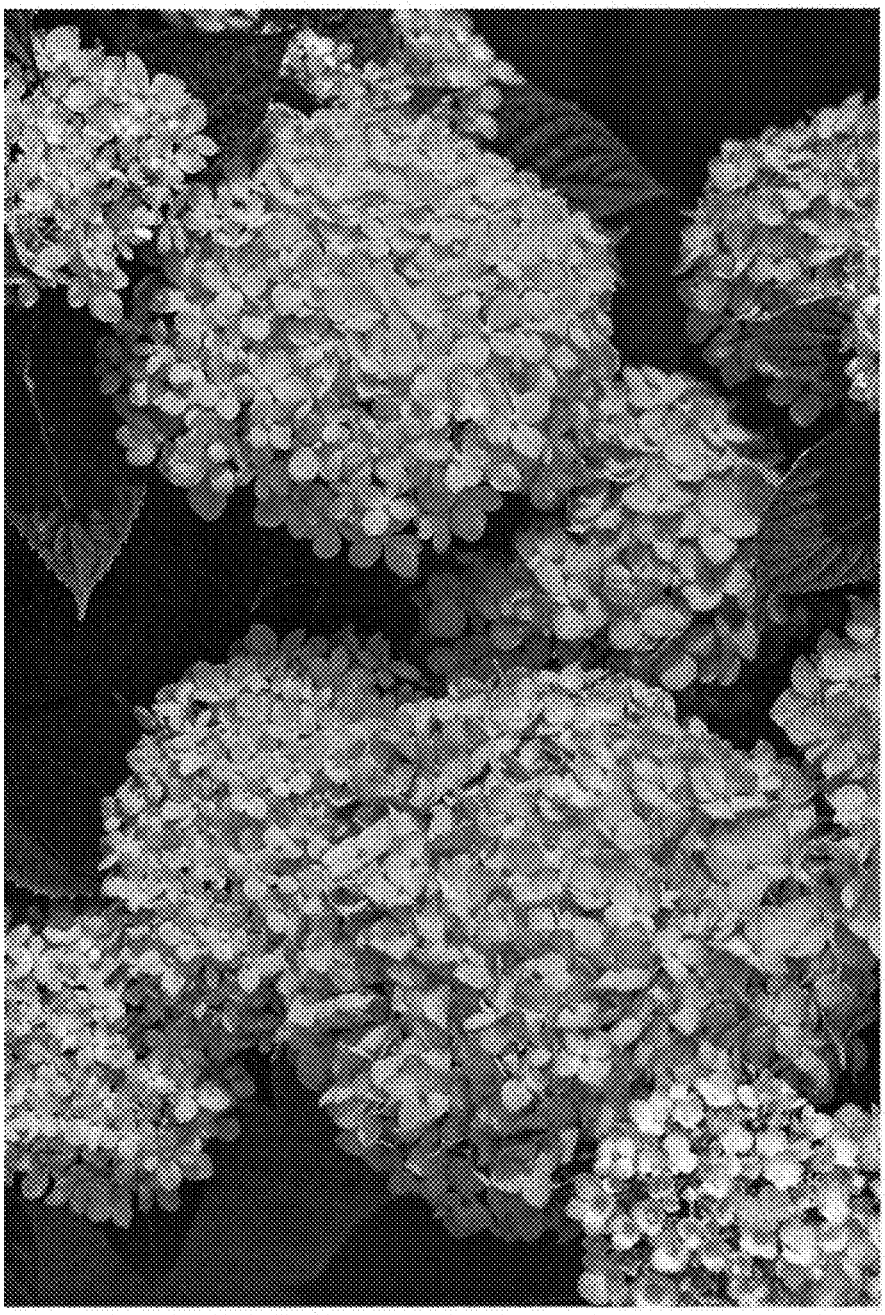

FIG. 2 illustrates in full color a close up view of multiple inflorescence. Inflorescences towards the right side of the figure show the more violet tones of plants produced in a more basic environment. Inflorescences towards the left are more pink, produced in a more acidic environment. Age of the plant photographed is approximately 2-3 years.

The photographs were taken using conventional techniques and although colors may appear different from actual colors due to light reflectance it is as accurate as possible by conventional photographic techniques.

DETAILED BOTANICAL DESCRIPTION

In the following description, color references are made to The 1996 Royal Horticultural Society Colour Chart except where general terms of ordinary dictionary significance are used. The following observations and measurements describe 'HMUPSI' plants grown in a double layered poly greenhouse, in Grand Haven, Mich., USA. The growing temperature ranged from approximately 18° C. to 27° C. daytime and 5° to 10° C. at night. Measurements and numerical values represent averages of typical plant types. Measurements were taken during July of 2015.

Botanical classification: *Hydrangea hybrida* 'HMUPSI'.

PROPAGATION

Time to initiate roots: Approximately 18 days at approximately 27° C.

Time to produce a rooted young plants: Approximately 60 days at approximately 27° C.

Root description: Thick and fine, freely root branching and dense, fibrous.

Propagation method: Softwood cuttings.

PLANT

Age of plant described: 2 to 3 years.

Pot size: 3 gallon.

Growth habit: Flowering perennial shrub, round. Semi-upright, non-climbing.

Overall plant shape: Round.

Height: 58 cm.

Plant spread: 91 cm.

Growth rate: Good.

Plant vigor: Good.

Branching characteristics: Opposite, basal branches, some pinching required. Non-fasciated.

Length of lateral branches/stems: Approximately 43 cm.

Number of lateral branches: 28.

Diameter of lateral branches: 6 mm.

Lateral branch shape and appearance: Round.

Lateral branch strength: Good.

Internode length: Average 7 cm.

Branch/stem color: Immature: Near RHS Yellow-Green 145B.

Branch/stem texture: Glabrous, lenticels not observed. Mature: Near RHS Yellow-Green 145B.

Branch angle: 0 to 20°.

Branch pubescence: No.

FOLIAGE

Leaf:

*Arrangement.*—Opposite.

*Average length.*—16 cm.

*Average width.*—10 cm.

*Shape of blade.*—Ovate, without lobes.

*Apex.*—Acuminate, average length 3 to 6 mm.

*Base.*—Rounded to obtuse.

*Margin.*—Serrate.

*Texture and appearance of top surface.*—Leathery, glossy.

*Texture and appearance of bottom surface.*—Glossy, coarse.

*Color.*—Solid, non-variegated. Young foliage upper side: Near RHS Yellow-green 144A. Young foliage under side: Near RHS Yellow-green 146B. Mature foliage upper side: Near RHS Green 137A. Mature foliage under side: Near RHS Yellow-green 146B.

*Venation.*—Type: Pinnate, Venation color upper side: Near RHS Yellow-green 145B. Venation color under side: Near Yellow-green 145C.

Petiole:

*Average length.*—3.0 cm.

*Diameter.*—4 mm.

*Color.*—Upper side: Near RHS Yellow-green 145B. Under side: Near RHA Yellow-green 145B.

*Texture upper side.*—Glossy, glabrous.

*Texture under side.*—Glossy, glabrous.

FLOWER

Bloom period:

*Natural season.*—Early Summer until Fall.

Inflorescence:

*Type.*—Mophead.

*Shape.*—Globular.

*Quantity of flowers per inflorescence.*—Fertile flowers, 90 approximate average, inconspicuous to slightly inconspicuous. Sterile Flowers, 414 approximate average.

*Persistent or self-cleaning.*—Self-cleaning.

*Fragrance.*—Lightly scented.

Panicle:

*Shape.*—Spherical, somewhat flattened.

*Height.*—6 cm.

*Diameter.*—15 cm.

Sterile flower:

*Bud shape.*—Obovate.

*Bud length.*—5.0 mm.

*Bud diameter.*—2.0 mm.

*Bud color.*—Acidic: Near RHS Red-Purple 73C. Basic: Near RHS Violet-Blue 98B.

*Flower aspect.*—Upright and outward.

*Flower shape.*—Cruciform.

*Flower length.*—12 mm.

*Flower diameter.*—18 mm.
*Flower depth.*—12 mm.
*Aspect.*—Facing upright and outward. Self cleaning.

Sterile flower petals:
*Petal arrangement.*—Whorl.
*Length of petal.*—Approximately 2 mm.
*Width of petal.*—Approximately 1 mm.
*Apex.*—Acute.
*Shape of petal.*—Ovate.
*Petal margin.*—Entire.
*Petal base.*—Obtuse/fused.
*Petal number.*—4.
*Petal texture.*—Smooth, upper and under side.
*Color.*—Upper surface at first opening: Acidic: Near RHS Red-Purple 73C. Basic: Near RHS Violet-Blue 98B. Upper surface at maturity: Acidic: Near RHS Red-Purple 73C. Basic: Near RHS Violet-Blue 98B. Under surface at first opening: Acidic: Near RHS Red-Purple 73C. Basic: Near RHS Violet-Blue 98B. Under surface at maturity: Acidic: Near RHS Red-Purple 73C. Basic: Near RHS Violet-Blue 98B. Color when fading: Both upper and lower surfaces continue with same coloration: Acidic: Near RHS Red-Purple 73C. Basic: Near RHS Violet-Blue 98B.

Sterile flower sepal:
*Arrangement.*—Whorl.
*Number.*—4.
*Shape.*—Obovate.
*Tip.*—Acute or obtuse.
*Base.*—Cuneate.
*Margin.*—Entire.
*Length.*—8 mm.
*Width.*—8 mm to 10 mm.
*Texture, upper.*—Smooth.
*Texture, lower.*—Smooth.
*Color.*—Upper surface at first opening: Acidic: Near RHS Purple-violet 81D and Violet-Blue 98A around margin. Basic: Near RHS Red-purple 73B. Upper surface at maturity: Acidic: Near RHS Purple-violet 81D and Violet-Blue 98A around margin. Basic: Near RHS Red-purple 73B. Under surface at first opening: Acidic: Near RHS Purple-violet 81D and Violet-Blue 98A around margin. Basic: Near RHS Red-purple 73B. Under surface at maturity: Acidic: Near RHS Purple-violet 81D and Violet-Blue 98A around margin. Basic: Near RHS Red-purple 73C. Fading to Upper surface: Acidic: Near RHS Purple-violet 81D and Violet-Blue 98A around margin. Basic: Near RHS Red-purple 73D. Fading to Under surface: Acidic: Near RHS Purple-violet 81D and Violet-Blue 98A around margin. Basic: Near RHS Red-purple 73D.

Sterile flower pedicel:
*Length.*—14 mm.
*Diameter.*—1 mm.
*Angle.*—Upright and outward.
*Strength.*—Good.
*Texture.*—Smooth.
*Color.*—Acidic: Near RHS Red-Purple 73D. Basic: Near RHS Purple-Violet 81D.

Fertile flower:
*Bud shape.*—Round to obovate.
*Bud length.*—2 mm.
*Bud diameter.*—2 mm.
*Bud color.*—Acidic: Near RHS Red-Purple 73C. Basic: Near RHS Violet-Blue 98B.
*Flower aspect.*—Upright and outward.
*Flower shape.*—Star-like, single.
*Flower length.*—5 mm.
*Flower diameter.*—4 mm.
*Flower depth.*—5 mm. Self-cleaning.

Fertile flower petals:
*Length of petal.*—2 mm.
*Width of petal.*—1 mm.
*Apex.*—Acute.
*Shape of petal.*—Ovate.
*Petal margin.*—Entire.
*Petal arrangement.*—Whorl.
*Petal number.*—5.
*Petal base.*—Rounded/obtuse.
*Petals fused.*—No.
*Petal texture.*—Smooth, upper and under side.
*Color.*—Upper surface at first opening: Acidic: Near RHS Red-Purple 73C. Basic: Near RHS Violet-Blue 98B. Upper surface at maturity: Acidic: Near RHS Red-Purple 74D. Basic: Near RHS Red-Purple 74D. Under surface at first opening: Acidic: Near RHS Purple 76B. Basic: Near RHS Purple 76B. Under surface at maturity: Acidic: Near RHS Red-Purple 66D. Basic: Near RHS Red-Purple 66D. Upper surface fading to: Acidic: Near RHS Red-Purple 74D, fading towards margin to 74C. Basic: Near RHS Red-Purple 74D, fading towards margin to 74C. Lower surface fading to: Acidic: Near RHS Red-Purple 75D, fading towards margin to 75B. Basic: Near RHS Red-Purple 75D, fading towards margin to 75B.

Fertile flower sepal:
*Arrangement.*—Whorl.
*Number.*—4.
*Shape.*—Deltate.
*Tip.*—Acute.
*Base.*—Ovate.
*Margin.*—Entire.
*Length.*—1 mm.
*Width.*—0.5 mm.
*Texture, upper.*—Smooth.
*Texture, lower.*—Smooth.
*Color, same for both acidic and basic conditions.*—Upper surface at first opening: Near RHS Purple 75B. Upper surface at maturity: Near RHS Purple 75B, blended with 75A. Under surface at first opening: Near RHS Purple 75C. Under surface at maturity: Near RHS Purple 75C, blended with 75B. Upper surface fading to: Near RHS Purple 75B, outwardly changing to 75A. Lower surface fading to: Near RHS Purple 75C, outwardly changing to 75B.

Fertile flower pedicel:
*Angle.*—15-90°.
*Strength.*—Good.
*Length.*—2.8 mm.
*Width.*—2.0 mm.
*Texture.*—Smooth.
*Color, same basic or acidic.*—Near RHS Yellow-Green 145C, blended with Red-Purple 73C.

REPRODUCTIVE ORGANS

Sterile flower:
Androecium:

*Stamen number.*—4 to 6.
*Filament length.*—1 mm.
*Filament color.*—Near RHS White 155A.
*Anther shape.*—Round.
*Anther color.*—Not accurately measurable with R.H.S. Chart.
*Anther length.*—Less 1 mm.
*Pollen amount.*—Scant.
*Pollen color.*—Not accurately measurable with R.H.S. Chart.

Gynoecium: Occurs in some flowers.
*Pistil number.*—1.
*Pistil length.*—1 mm.
*Stigma shape.*—Lobed.
*Stigma color.*—Near RHS Red-Purple 74C.
*Style length.*—1 mm.
*Style color.*—Near RHS Red-purple 74C.
*Ovary color.*—Near RHS White 155B.

Fertile flower:
*Stamen number.*—5.
*Filament length.*—Average 2.75 mm.
*Filament color.*—Near RHS White 155A.
*Anther shape.*—Oblong and irregularly lobed.
*Anther length.*—1 mm.
*Anther color.*—Near RHS Greyed-green 197D.
*Pollen amount.*—Scant.
*Pollen color.*—Near RHS White 155B.

Gynoecium:
*Pistil number.*—1.
*Pistil length.*—5 mm.
*Stigma shape.*—Lobed.
*Stigma color.*—Red-Purple 74C.
*Style length.*—2 mm.
*Style color.*—Near RHS Red-Purple 74C.
*Ovary color.*—Near RHS White 155D.

OTHER CHARACTERISTICS

Disease resistance: Neither resistance nor susceptibility to diseases or pests has been observed in this variety.

Cold tolerance: −31° C. to 38° C.

Fruit/seed production: 1000s of seeds. Seeds very small, dust-like. Too minute to measure accurately with an R.H.S. Chart.

What is claimed is:

1. A new and distinct cultivar of *Hydrangea* plant named 'HMUPSI' as herein illustrated and described.

* * * * *